United States Patent [19]
Vonk et al.

[11] Patent Number: 5,293,879
[45] Date of Patent: Mar. 15, 1994

[54] SYSTEM AN METHOD FOR DETECTING TREMORS SUCH AS THOSE WHICH RESULT FROM PARKINSON'S DISEASE

[75] Inventors: B. F. M. Vonk, Wehl; Eugenio Johannes W. Van Someren, Amsterdam, both of Netherlands

[73] Assignee: Vitatron Medical, B.V., Netherlands

[21] Appl. No.: 763,621

[22] Filed: Sep. 23, 1991

[51] Int. Cl.⁵ .............................................. A61B 5/00
[52] U.S. Cl. ................................... 128/782; 364/508; 364/413.05
[58] Field of Search ............... 128/782, 779, 784, 739; 364/508, 413.01, 413.02, 413.05; 604/50; 73/570, 579

[56] References Cited

U.S. PATENT DOCUMENTS

| | | | |
|---|---|---|---|
| 3,163,856 | 12/1964 | Kirby | 128/782 |
| 4,112,926 | 9/1978 | Schulman et al. | 128/782 |
| 4,117,834 | 10/1978 | McPartland et al. | 128/782 |
| 4,195,643 | 4/1980 | Pratt, Jr. | 128/779 |
| 4,306,291 | 12/1981 | Zilm et al. | 128/739 |
| 4,353,375 | 10/1982 | Colburn et al. | 128/782 |
| 4,444,205 | 4/1984 | Jackson | 128/782 |
| 4,520,674 | 6/1985 | Canada et al. | 364/508 |
| 4,822,337 | 4/1989 | Newhouse et al. | 604/50 |
| 4,951,674 | 8/1990 | Zanakis et al. | 128/653 R |
| 5,031,614 | 7/1991 | Alt | 128/419 OPG |

FOREIGN PATENT DOCUMENTS

| | | |
|---|---|---|
| 3446338 | 7/1986 | Fed. Rep. of Germany . |
| 3916500 | 5/1989 | Fed. Rep. of Germany . |
| 566559 | 8/1977 | U.S.S.R. ............................... 128/782 |
| 632345 | 11/1978 | U.S.S.R. ............................... 128/782 |

OTHER PUBLICATIONS

Zilm et al. "The Nature . . . Tremor", IEEE Transations on Biomedical Engineering, vol. BME 26, No. 1, Jan. 1979, pp. 3-10.

Pau, "Data Compression . . . Examination", Medical and Biol. Eng. and Comput. vol. 15, May 1977, pp. 292-297.

Colburn et al., "An Ambulatory Activity Monitor . . . Memory", ISA Transactions, vol. 15, No. 2, pp. 149-154 (1976).

Primary Examiner—Stephen C. Pellegrino
Assistant Examiner—Guy V. Tucker
Attorney, Agent, or Firm—Woodcock, Washburn, Kurtz, Mackiewicz & Norris

[57] ABSTRACT

A system and method are provided for accurate determination of various tremors and movements derived from Parkinson's Disease and other causes. Movement signals are generated by an accelerometer, the movement signals being analyzed to determine whether they are in a predetermined frequency range, and when there occurs an uninterrupted series of such movement signals that are within the frequency range. By determining when these two criteria are met, tremor signals are reliably discriminated from other activity signals. The system includes circuitry for collecting and storing data concerning the timing of tremor occurrences, the timing of other activity occurrences, and amplitude data concerning tremor occurrences.

20 Claims, 6 Drawing Sheets

SYSTEM AN METHOD FOR DETECTING TREMORS SUCH AS THOSE WHICH RESULT FROM PARKINSON'S DISEASE

BACKGROUND OF THE INVENTION

1. Field of the Invention

This invention relates to a system and method for detecting tremors such as derived from Parkinson's Disease and, more particularly, to such systems and methods which involve detecting movement and processing signals representative of movement so as to discriminate tremor-derived signals from activity and non-tremor signals.

2. Description of the Prior Art

Monitoring of patients to determine the occurrence of Parkinson's tremors is known in the art, although very few long-term tremor registrations have been reported in the literature. The literature has reported 24-hour recordings, but no easily applicable and useful tool has been provided. Prior known monitoring systems generally comprise some arrangement for taking an electromyogram or accelerometer signal and transmitting received signals and/or data to an on-line recorder. Data analysis normally takes place off-line, which is very time consuming. Other systems, so-called actometers, generally count movements of a patient's limb, e.g., arm or leg, but do not accurately discriminate between movements representative of tremors and those representative of other forms of movement or activity. Moreover, no index of the average acceleration of movements is given in such a system. See, for example, U.S. Pat. No. 4,353,375, which discloses the general concept of detecting arm or leg movement, but which does not suggest how to separate out tremor signal from other activity signals.

Our investigations have confirmed the shortcomings of the prior art. We have registered movements in ten Parkinsonian patients (both sexes, ages 43 to 89) and twenty healthy volunteers (both sexes, ages 26 to 67). Each patient wore an accelerometer on the wrist, the output of which was continuously recorded on a portable analog instrumentation recorder for 24 hours. Recordings were ambulant, and no restrictions on movements were made. Data were sampled with a frequency of 100 Hz for off-line computer analysis. The attempt to discriminate tremor from non-pathological movements by frequency was not satisfactory: fast Fourier transforms showed that the movement patterns overlapped in frequency range. Thus, there remains a need for a system and method which reliably discriminates reliable tremor signals from activity and non-tremor-induced signals. There further remains a need in the art for obtaining data by which tremor activity can be classified and analyzed so as to optimally indicate desired treatment, i.e., drug level setting by the physician automatic drug injection.

SUMMARY OF THE INVENTION

It is a primary object of this invention to provide a system and method for monitoring tremors of Parkinson's Disease and the like, the system having capability for discriminating against activity and other non-tremor signals so as to provide signals reliably reflective of tremor. As used in describing this invention, tremor also includes so-called motor slowing (bradykinesia) and motor acceleration (hyperkinesia) as observed in children.

It is a further object to process the tremor signals so as to obtain accurate tremor histories, in terms of signal characteristics and timing of tremor signals, and to provide for patient treatment as a function of such histories.

It is a still further object to provide the basic design components of a system for ambulatory monitoring of Parkinsonian tremors, which can be adapted into a miniaturized wristwatch-type device worn by the patient.

Our invention is based upon the observation that while non-tremor signals overlap the tremor frequency range (about 3–12 Hz), it is improbable that a series of signals within the tremor range would represent anything but a tremor, so long as the series exceeds a critical length. Thus, for example, if a critical series length (CSL) of eight or more consecutive signals are detected within the tremor range, without any intervening periods, then the signal can reliably be recognized as a tremor. In normal limb movement, a series of 3–12 Hz periods will seldom reach this CSL, while most series in tremor will exceed the CSL.

In accord with the above objects, there is provided by this invention a system and method for monitoring tremors in the limb of a patient, the system having an accelerometer or like means for detecting limb movements and for generating movement signals representative thereof, and process circuitry for programmed processing of the signals with means to filter out signals outside of the frequency range of the tremor signals. The system further comprises analyzing means, preferably involving a microcontroller, for determining the half-cycle time periods of the movement signals as well as a representation of signal amplitude, and means for identifying a tremor as constituting a series of consecutive signals having a given range of time periods within a programmed range. For example, the system may look for movements having time periods within the range of about 40–170 ms, and for at least twelve consecutive such periods. Further, in a preferred embodiment, tremor amplitude information is stored, along with histogram data relating to tremor and non-tremor activity. The system comprises utilizing tremor amplitude and timing data, as well as activity data, for providing indications of patient treatment. The combination of discriminating out many of the non-tremor signals, determining the occurrence of consecutive signals within the tremor frequency range, and storage and processing of such tremor-range signals, results in a system with enhanced ability for reliably detecting movement and tremor fluctuations as seen, for example, in patients with Parkinson's disease. The invention is illustrated with an embodiment that includes external processing capabilities, such as a portable computer, but also embraces a portable device of wristwatch size, which can automatically control a dispensing unit such as an implantable pump. The invention is illustrated with respect to Parkinsonian tremors, but is equally applicable to other types of tremors.

DESCRIPTION OF THE PREFERRED EMBODIMENTS

Figure 1:
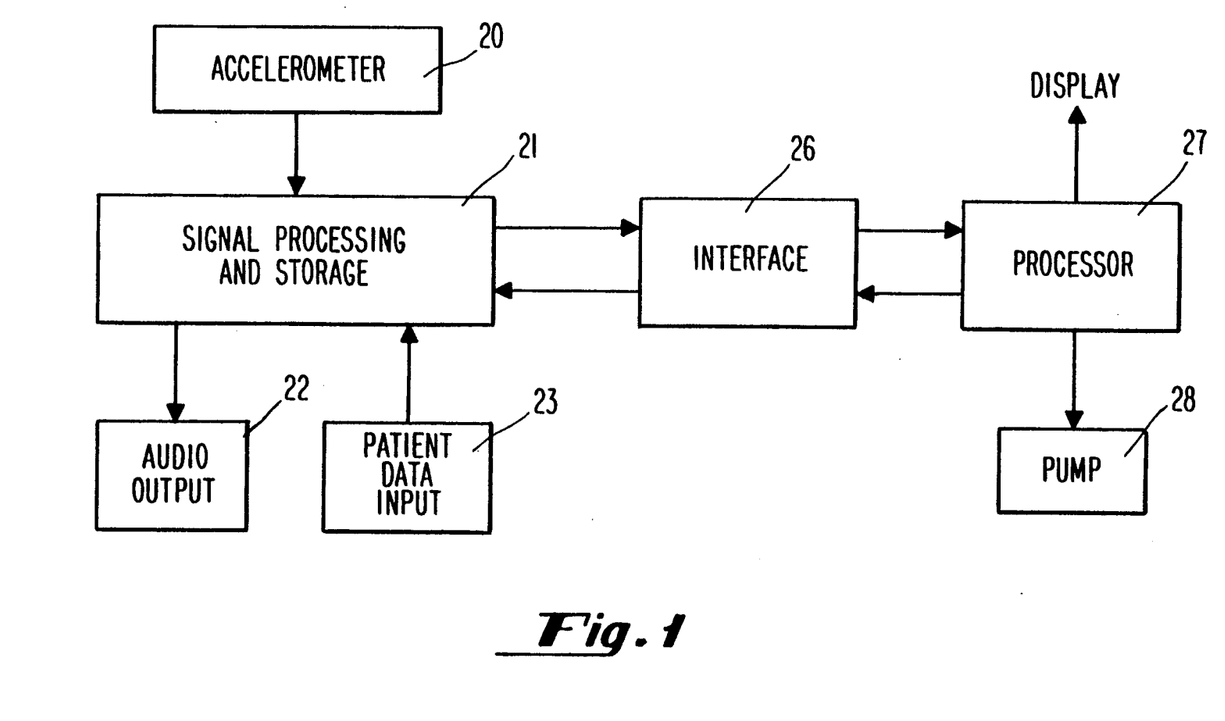
FIG. 1 is block diagram showing the primary system components of this invention.

Referring now to FIG. 1, there is shown an overall block diagram of the system of this invention. Block 20 represents an accelerometer device package with interface electronics, which is suitably attached to the patient's arm or other limb. The accelerometer passes its signal to the signal processing and storage apparatus 21, which generally comprises hardware and software for processing the accelerometer output, as well as memory storage for holding algorithm software and stored data obtained from the accelerometer. In practice, apparatus 21 may be a portable processing unit packaged separately from the acceleometer sensor 20. However, the invention embraces packaging all of this apparatus in a wristwatch-like device, capable of registering and storing tremor data on a fixed interval, e.g., hourly basis, over a duration of several weeks.

Further as shown in FIG. 1, there is shown an audio output 22 which receives output signals from block 21, and provides an audio output of a predetermined nature to the patient. The audio output may, for example, signal to the patient when the battery is low, or may provide coded signals representing a variety of device conditions. Patient data input block 23 represents a means whereby the patient can transmit signals to device 21, either for immediate use or storage. Interface 26 is in two way communication with device 21, and in turn is in two way communication with processor 27, which may suitably be a personal computer. The personal computer can be used to program processing variables in apparatus 21, and may also be used in a situation where the device is interrogated to read out data that has been stored over a duration of time, for analysis and display. The computer may further be used to control a pump 28, which is used for dispensing medicine such as L-Dopa at an optimum rate and amount as determined by processing of the patient data. The invention also embraces the design of processor 27 as a dedicated unit for carrying out the treatment analysis, in which case it may be incorporated into a single miniaturized system package worn by the patient. In such a case, processor 27 may directly control an implantable pump 28.

Detection and discrimination of the abnormal movements constituting a tremor caused by Parkinson's Disease, or another cause as contrasted to normal activity movements, is based primarily on two criteria, leading to a period amplitude sequence analysis (PASA). It is known that the dominant frequency for Parkinson's disease, for example, varies between 3 and 7 Hz for a rest tremor, and up to 12 Hz for a postural tremor. However, as noted above, a tremor cannot be reliably distinguished from normal movements on the basis of frequency above. Such tremors do differ from normal movements in the number of repetitions of signals within a confined frequency band. We define tremor operationally as a sequence of repetitive movements both within a given frequency band and enduring for a critical length of time.

In the logical analysis of tremor signals according to the invention, first, the period time of the incoming signal is specified to be between certain limits, e.g., about 40-170 ms. Note that these durations, representing half cycles as seen in curve (a) of FIG. 2A, correspond to frequencies of about 12 and 3 Hz respectively, i.e., a range of 3-12 Hz.

In addition, a further basic step is taken, namely carrying out of a sequence analysis, to count the number of repetitions (without break) that meet the period criteria. For example, if at least twelve half-periods are uninterrupted by "rest" or "activity", these sequences are classified as tremors. Depending on the frequency of the tremor, this criterion requires an uninterrupted tremor signal somewhere between about 0.48 seconds (for a 12.5 Hz tremor) and 2.04 seconds for a 2.94 Hz tremor.

Figure 2A:
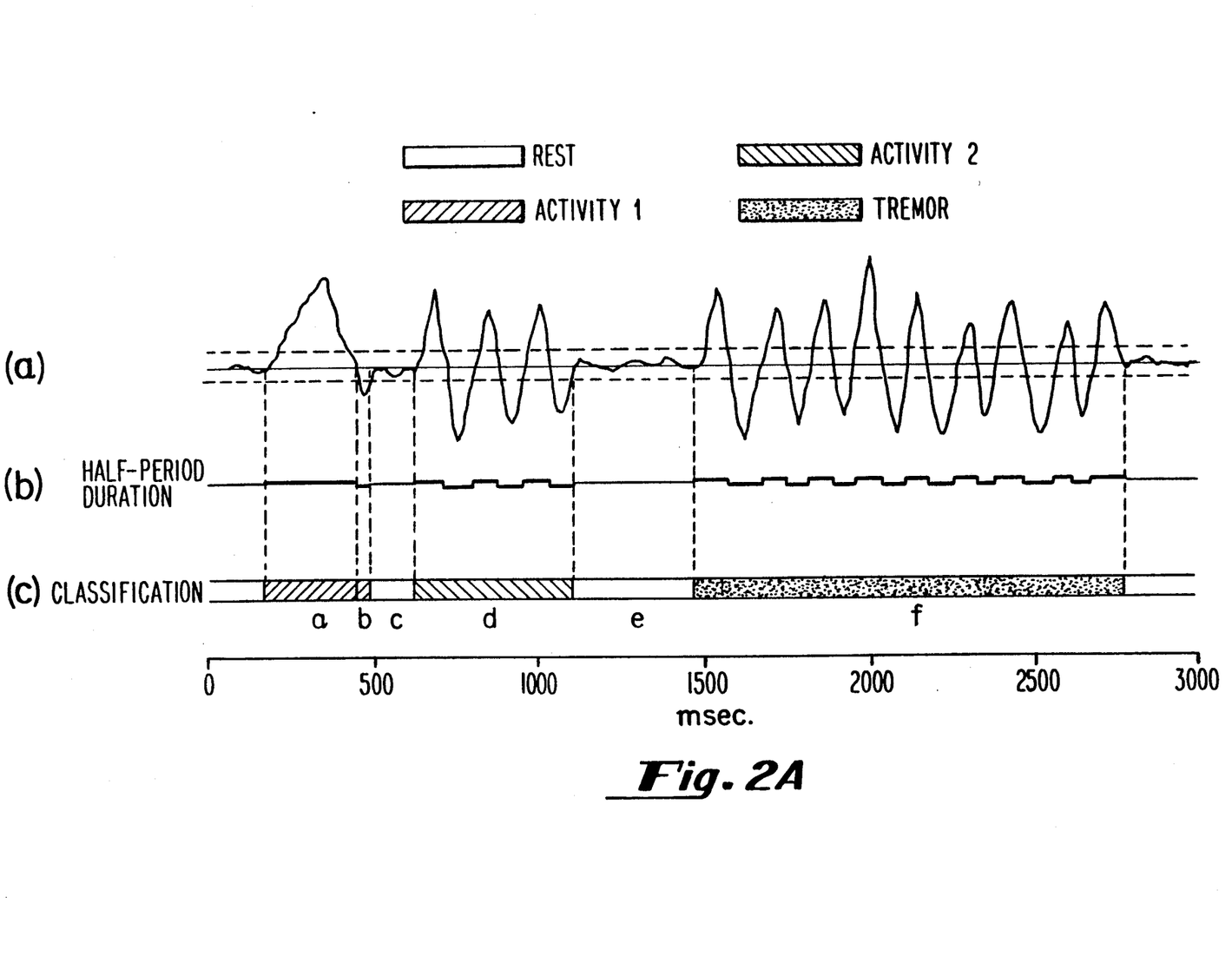
FIG. 2A is a graph illustrating a limb movement signal over 3 seconds and the logical analysis for distinguishing rest, activity and tremor.

Still referring to FIG. 2A, the signal is shown with respect to a zero reference line, and with respect to dashed threshold lines. Zero crossings are used to reduce the signal to durations and maximum absolute values between successive zero crossings, i.e., half-periods and their amplitudes. Plus and minus thresholds are arbitrarily established at low levels, to avoid scoring of minor fluctuations around zero as movement or tremor. Thus, whenever the signal between two or more zero crossings does not exceed a threshold, as seen at episodes (c) and (e) of curve (c), it is determined to be "rest." Of the remaining signals, the half-periods with a duration between 40 and 170 ms are selected as indicated at line (b). Half-periods with a shorter or longer duration (as seen at (b) and (a) respectively in line (c)) are classified as "activity 1." The next step, based on the above assumed characteristics of tremor and other movements, is to select from the remaining signals only sequences of at least twelve half-periods uninterrupted by "rest" or "activity 1." These sequences are classified as tremor, as seen at (f) on line (c) of FIG. 2A, while shorter sequences are classified as "activity 2", as seen at (d) on line (c). From these classifications, total time of epochs determined as tremor, activity 1 and/or activity 2 can be determined, e.g., hourly, as well as the average amplitude of signal during these epochs and the mean duration of the epochs.

Figure 2B:
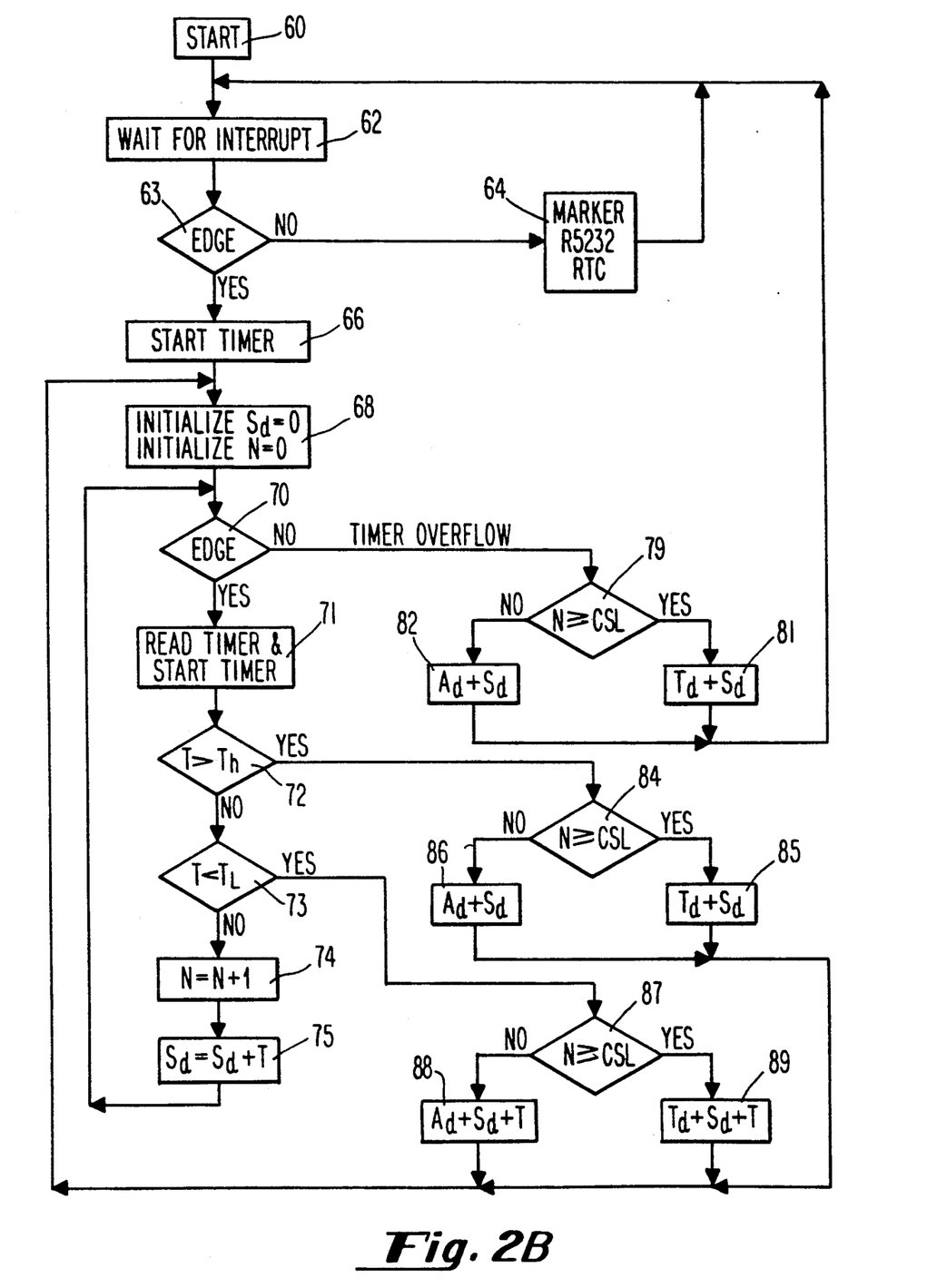
FIG. 2B is a simplified flow diagram of the logical steps for distinguishing these states.

Referring now to FIG. 2B, there is shown a flow diagram illustrating an algorithm for carrying out the logical steps in this invention in determining a tremor. In FIG. 2B, the following symbols are used:

T = measured half-period time
Sd = serial duration of half-periods
Ad = total duration of activity
Td = total duration of tremor
N = number of cycles
CSL = critical series length
$T_h$ = programmable high time for half-period (e.g., 170 ms)
$T_l$ = programmable low time for half-period (e.g., 40 ms)

The algorithm starts as indicated at 60, and waits for an interrupt at 62. Upon an interrupt, it is determined at 63, whether the edge of a half signal, or crossover has been detected. If no, the interrupt pertains to another matter, and the routine switches to interrogate the marker, RS 232 or RTC. If yes, the routine proceeds to 66, where the timer is started, to time out the interval T following the start of the signal. At 68, Sd and N are initialized to zero. At 70, it is determined whether another edge has been detected, or whether there has been timer overflow, meaning that a period has elapsed without any crossover. If another signal edge is detected, then at 71 the timer is read and restarted. The elapsed time T of the timer, is compared at 72 to $T_h$, and at 73 to $T_1$. If T is within the two limits, then at 74 N is incremented by 1, and the serial duration of half-periods (Sd) is incremented by the time of the interval just elapsed, i.e., T. The routine then loops back to 70 to wait for the next edge.

Referring back to block 72, if T is greater than $T_h$ (representing a frequency lower than the low frequency limit), the program branches to 84 where it is determined whether N has reached CSL. If yes, this means that a tremor has been detected, and the total tremor duration is incremented by Sd. If no, meaning activity but no tremor, then the total activity duration is incremented by Sd. Likewise, at 73, if T is less than $T_1$, the program branches to 87 where again it is determined whether N is equal to or greater than CSL. If yes, total duration of tremor is incremented by the accumulated Sd plus the most recent interval T; if no, total duration of activity is incremented by Sd+T.

Figure 3:
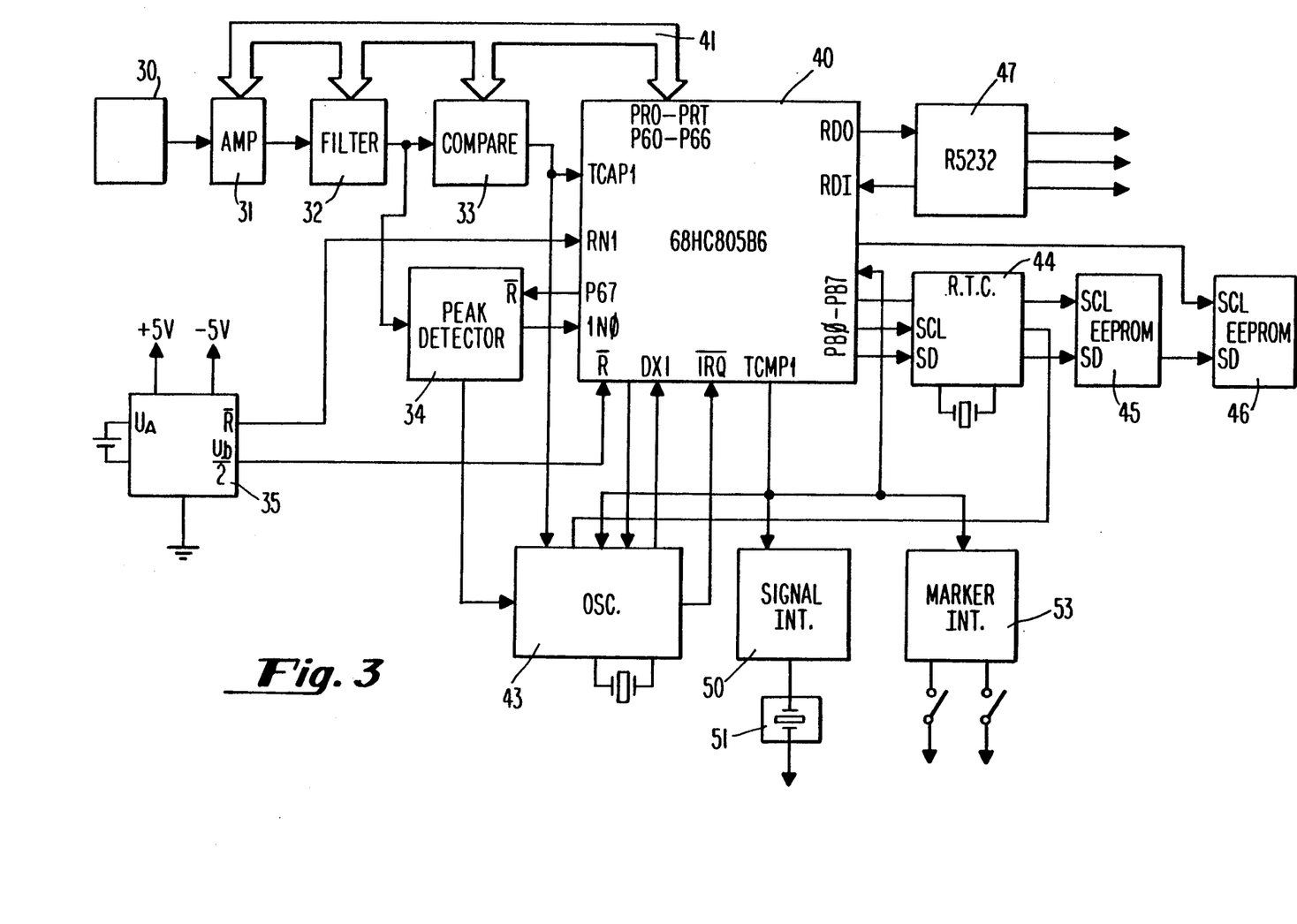
FIG. 3 is a block diagram showing the primary hardware components of the apparatus of this invention.

Referring now to FIG. 3, the accelerometer unit is shown at 30. The accelerometer may be a model 12 PICOCHIP TM, made by Endevco. This is a miniature accelerometer based on bimorph bender technology, and has a size of about 3.6×4.6×1.5 mm. The sensor is basically a charge generating device which is capable of detecting arm movements. The charge generates a voltage across a resistor when there is a movement of the arm; this voltage is amplified by about 100, and buffered by a low power operational amplifier, before outputting to the following processing circuitry. The accelerometer and interface electronics are mounted in a metal case, connected to electrical ground. The output from accelerometer 30 is connected to a programmable amplifier 31, which receives program signals from microcontroller 40 across bus 41. Amplifier 31 may, for example, have eight programmable values, 5× to 40×, providing an overall gain in the range from 500 to 4000. These programmable values are held by respective port lines of the microcontroller 40.

The output of amplifier 31 is connected to a programmable filter 32 which has programmable low and high pass roll off points. The low pass point is suitably programmable to values between 0.5 and 5 Hz with steps of 0.5 Hz. Respective port lines of the microcontroller are used to provide the program values. In practice, the high pass point is programmable between about 8 and 12 Hz in steps of 0.5 Hz. The filter roll off characteristics are 12 dB/oktaaf. By this means, the filter passes only signals within the desired period range, e.g., 3 to 8 Hz.

The output from the filter is connected through to comparator 33, which suitably operates as a cross-over detector. As seen also in connection with FIG. 3, the output of the comparator produces a pulse for the time period when the signal has exceeded a given positive threshold above reference value, and likewise when the negative swing of the signal exceeds a corresponding negative value. The comparator is programmable through controller 40 to eight different detection levels, ranging from 0.25 v to 2 v, which values are provided by respective port lines of the microcontroller. The output pulses from the comparator 33, which represent signals within the programmed period (frequency) range, are inputted to microcontroller timer input TCAP1. The output of filter 32 is also connected to a peak detector 34 for measuring peak values of the filtered signals. At the end of every incoming event, whether tremor or activity, the peak value is converted by an AD convertor of the microcontroller, and such values are averaged over a predetermined programmable period and stored in an EEprom. The peak detector is reset after an A/D conversion by a logic signal from an appropriate port line of the controller.

The microcontroller is suitably a 68HC805B6. This controller is indicated because of its low power consumption, 6 k EEprom program memory, on-board 8 channel A/D convertor, serial interface capability and flexible timer/comparator system. Because the processor is a DC-type, its clock frequency can go down to 0 Hz. For this reason, the clock signal is generated externally by oscillator circuit 43, which provides a 76.8 kHz signal having a good time base for the serial interface (1200 Baud) and a good measuring value for the timer input. The clock signal can be put on hold by a logic signal on one of the microcontroller lines. The clock can be started by several events; a signal from the comparator, a marker input, or a real time clock overflow can start up the clock again.

Block 44 represents a real time clock, which operates separately from the microcontroller so as not to disturb normal microcontroller routines. The RTC has its own 32.768 Hz crystal; and has an interrupt capability for interrupting the processor every programmable period, e.g., every hour or half hour, to store total counted data in EEprom 45. The RTC generates an interrupt vector which is connected to a suitable line of the microcontroller. A second EEprom 46 is also utilized, as shown, such that main storage of data is provided by two 2 k byte EEproms.

Interface unit 47 is preferably an RS232 transceiver used to connect the device which is mounted on the patient to processor or computer 27.

Still referring to FIG. 3, power supply 35 generates required +5 and −5 voltages for the circuitry out of a 9 volt battery, and also generates a Ub/2 signal for measuring of actual battery voltage. This voltage is measured suitably every hour by the microcontroller on an analog line of the microcontroller. The power supply circuit also generates a power up reset signal, as indicated. A sound interface 50 is utilized as a driver for piezo electric tone generator 51. Frequencies for several tones are generated by the programmable timer TCMP1 of the microcontroller. For example, when the value of Ub/2 reaches a predetermined level, the microcontroller provides an alert signal through sound interface 50 and generator 51. The length and frequency of the signal are programmable. There is also provided a marker interface 53, which holds information about the switch positions of switches indicated as 1 and 2. These marker switches can be used by the patient to signal predetermined occurrences such as medicine use, sleep time, eat time, etc. The marker interface is connected through to suitable lines of the microcontroller, and can be reset by a logic signal on another one of the lines.

The software for operating the microcontroller contains standard routines for handling the following:

1. Interrupt handling
   a. Timer interrupt handling
   b. RTC interrupt handling
   c. Marker interrupt handling
2. A/D Conversion
3. Oscillator start and stop
4. Sound generation routine 5. Serial data storage routine, i.e., transferring data relating to tremor identification, detected amplitude information, and time of tremor from microcontroller to EEprom.

6. Communication routine for the RS232 interface.

Figure 4A:
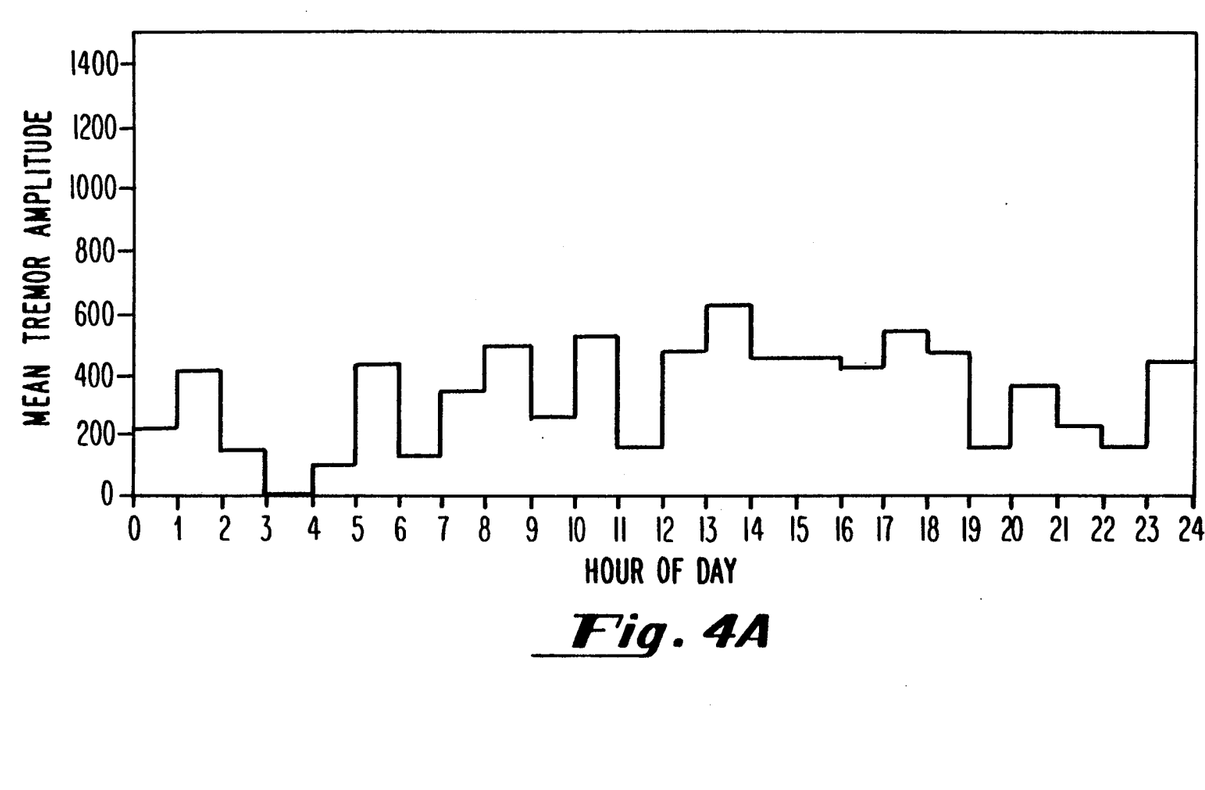
FIG. 4A is a representation of a histogram showing mean tremor amplitude as obtained in the system of this invention.
Figure 4B:
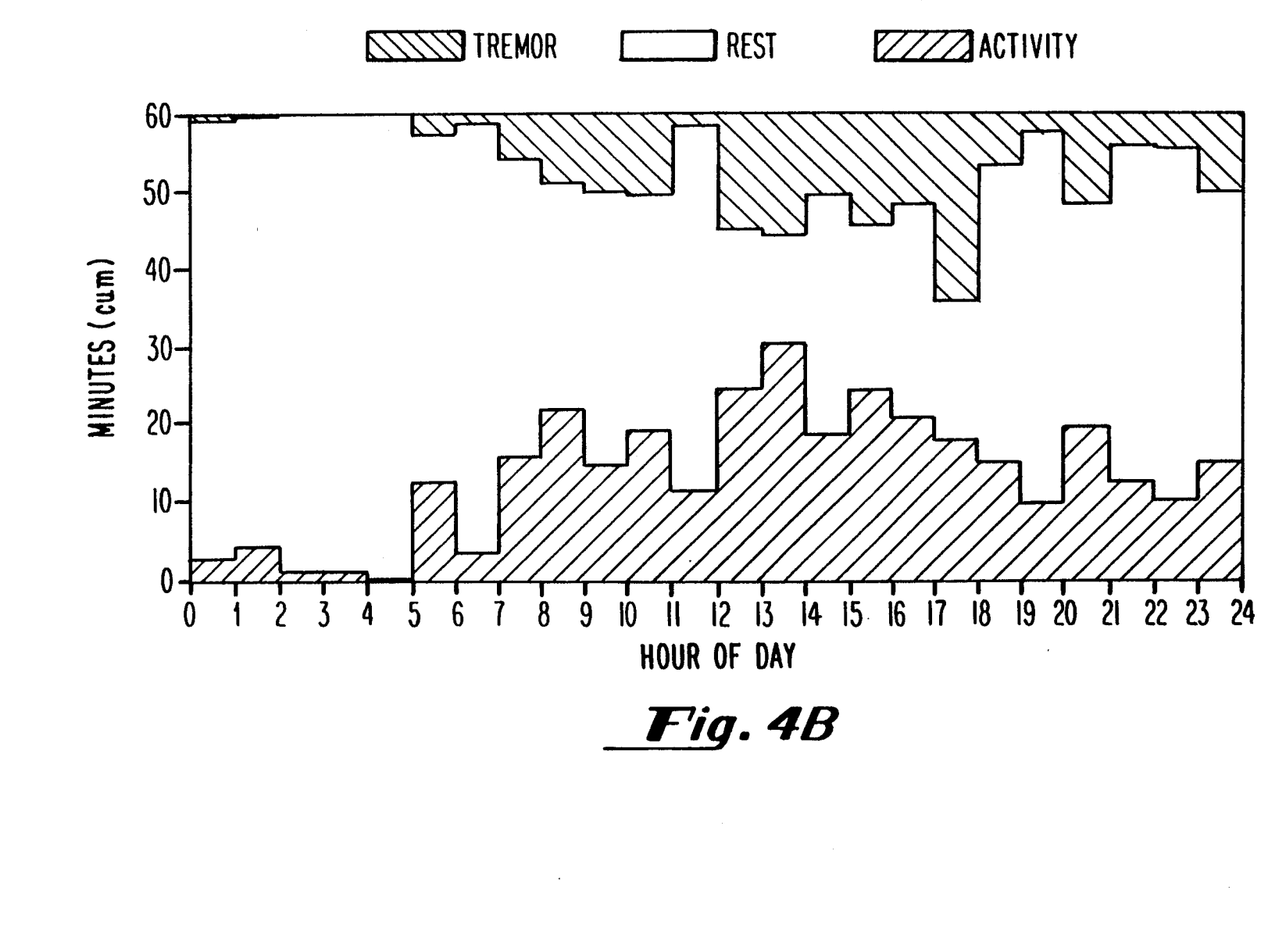
FIG. 4B is a graph illustrating histogram data representing tremor and activity occurrence as obtained with the system of this invention.

The system and method of this invention further encompass techniques for evaluating the tremor data, to determine desired treatment. Referring to FIGS. 4A and 4B, there are shown representative histograms which are determined, suitably by personal computer 27, and displayed on an appropriate display, to provide information from which a physician may select treatment. In FIG. 4A, a histogram of mean tremor amplitude is presented, and the physician evaluates this pattern of mean amplitude as a function of time of day in order to determine appropriate treatment. In FIG. 4B, there is shown a dual histogram of tremor and activity, with the remaining time being classified as rest. Upon the presentation of this histogram, the physician can determine appropriate treatment as a function of the time of sensed tremors, or as a function of the time of the tremors and the time of other sensed activity. Of course, for a miniaturized totally portable system worn by the patient, where the microprocessor or other dedicated circuitry is part of the package worn directly by the patient, other criteria for evaluating the data may be used so as to directly control a pump 28 or other suitable treatment rendering apparatus.

It is to be understood that the system and method of this invention are not limited in scope to the specific embodiment illustrated. Thus, while the specific microcontroller illustrated can carry out the functions of counting pulses, determining the number of pulses in a series, and storing pulse amplitude values, these and similar functions can be carried out by other well known forms of hardware and/or software. Also, while the preferred embodiment is a wristwatch-like package which carries out all the processing, the invention embraces other forms, e.g., separate accelerometer and processing units.

As used in the claims, the terms "period" and "half-period" are the same, i.e., the pulse formed from a positive or negative portion of a signal, between zero crossings, can be described as having a period or half period T.

What is claimed:

1. A system for monitoring tremors in the limb of a patient, comprising
    means for detecting limb movements and for generating signals representative of said limb movements,
    analyzing means for analyzing said signals to determine signal periods,
    storage means for storing signal period criteria, said criteria comprising data representing a range of signal periods within about 40-170 ms and characteristic of tremors, and a number greater than zero corresponding to a minimum number of consecutive signals with periods in said range which repeat uninterruptedly without intervening periods, and
    determining means for determining when said signal periods of said signals are within said range and for determining when said signals with periods within said range repeat at least said minimum number of times without interruption, whereby tremor occurrences are detected.

2. The system as described in claim 1, wherein said number is eight.

3. The system as described in claim 1, comprising means for generating and storing tremor histogram data from said signals.

4. The system as described in claim 1, comprising amplitude means for determining the amplitude of said signals and for generating and storing amplitude data representative of said amplitudes.

5. The system as described in claim 4, wherein said amplitude means comprises means for generating peak amplitude data corresponding to said signals.

6. The system as described in claim 4, comprising treatment means for indicating treatment as a function of said signal amplitude data.

7. The system as described in claim 1, comprising time means for generating and storing time signals corresponding to the time of detected tremors.

8. The system as described in claim 7, comprising treatment means for indicating treatment as a function of said time signals.

9. The system as described in claim 8, wherein said treatment indicating means comprises means for determining data representative of normal patient activity and for indicating treatment as a function of the timing of tremors and the timing of normal activity.

10. The system as described in claim 1, further comprising marker interface means for enabling the patient to input time data into said system.

11. The system as described in claim 1, further comprising sound output means for outputting an audio signal representative of a detected condition of said system.

12. The system as described in claim 1, comprising storage means for storing tremor data representative of said tremor occurrences, a pump for introducing a medicinal liquid into said patient for treatment of tremors, and means responsive to said stored data for operating said pump.

13. The system as described in claim 1, comprising a programmable filter for filtering said generated representative signals so as to pass only signal frequencies within a programmable range.

14. The system as described in claim 1, wherein said detecting means comprises an accelerometer.

15. The system as described in claim 1, comprising storage means for storing tremor data representative of said tremor occurrences, computer means for processing said tremor data, and linking means for linking said stored tremor data to said computer means.

16. The system as described in claim 1, comprising threshold determining means for determining when signals being analyzed do not exceed a predetermined minimum amplitude, indicating a rest period.

17. The system as described in claim 1, wherein said determining means comprises rest means for determining when there is an interruption of signals having signal periods within said range, thereby indicating rest or inactivity.

18. A method of detecting a tremor of an ambulatory patient, comprising
    establishing frequency and duration criteria applicable to the movements of a tremor to be detected,
    continuously obtaining signals representative of limb movement of said patient,
    determining when said signals meet said frequency criterion, and
    determining when said signals meeting requirements of said frequency criterion continue substantially without any intervening periods over a time period corresponding to said duration criterion.

19. A system for detecting a tremor of a patient, said system having means for continuously obtaining and analyzing signals representative of limb movement of said patient, characterized by means for storing frequency and duration criteria applicable to the movements of a tremor to be detected, first means for determining when said signals meet requirements of said frequency criterion, and second means for determining when said signals meeting requirements of said frequency criterion continue substantially without any intervening periods over a time period corresponding to said duration criterion.

20. The system as described in claim 19, comprising accumulating means for accumulating determined duration time.

* * * * *